United States Patent [19]

Hershberg

[11] Patent Number: 4,624,918

[45] Date of Patent: Nov. 25, 1986

[54] PURIFICATION PROCESS FOR HEPATITIS SURFACE ANTIGEN AND PRODUCT THEREOF

[75] Inventor: Robert D. Hershberg, San Franciso, Calif.

[73] Assignee: Genentech, Inc., South San Francisco, Calif.

[21] Appl. No.: 629,295

[22] Filed: Jul. 9, 1984

[51] Int. Cl.$^4$ .................... C12P 21/00; A61K 39/29
[52] U.S. Cl. .......................... 435/68; 424/88; 424/89
[58] Field of Search ................ 424/88, 89; 435/68

[56] References Cited

U.S. PATENT DOCUMENTS

| | | | |
|---|---|---|---|
| 3,994,870 | 11/1976 | Neurath et al. | 424/89 |
| 4,088,748 | 5/1978 | McAleer et al. | 424/89 |
| 4,181,713 | 1/1980 | McAleer et al. | 424/89 |
| 4,186,193 | 1/1980 | McAleer et al. | 424/89 |
| 4,271,145 | 6/1981 | Wands et al. | 424/85 |
| 4,349,539 | 9/1982 | Wampler | 424/89 |
| 4,442,205 | 4/1984 | Hamer et al. | 424/89 |

FOREIGN PATENT DOCUMENTS

| | | |
|---|---|---|
| 0062574 | 10/1982 | European Pat. Off. |
| 0072318 | 2/1983 | European Pat. Off. |
| 0101617 | 2/1984 | European Pat. Off. |

Primary Examiner—Blondel Hazel

[57] ABSTRACT

A method for the purification of hepatitis B surface antigen from recombinant cell culture comprising concentrating the antigen, precipitating the antigen, purifying the antigen by adsorption to an immunoaffinity column, eluting the antigen and fractionating the antigen on an anion exchange bed.

2 Claims, 2 Drawing Figures

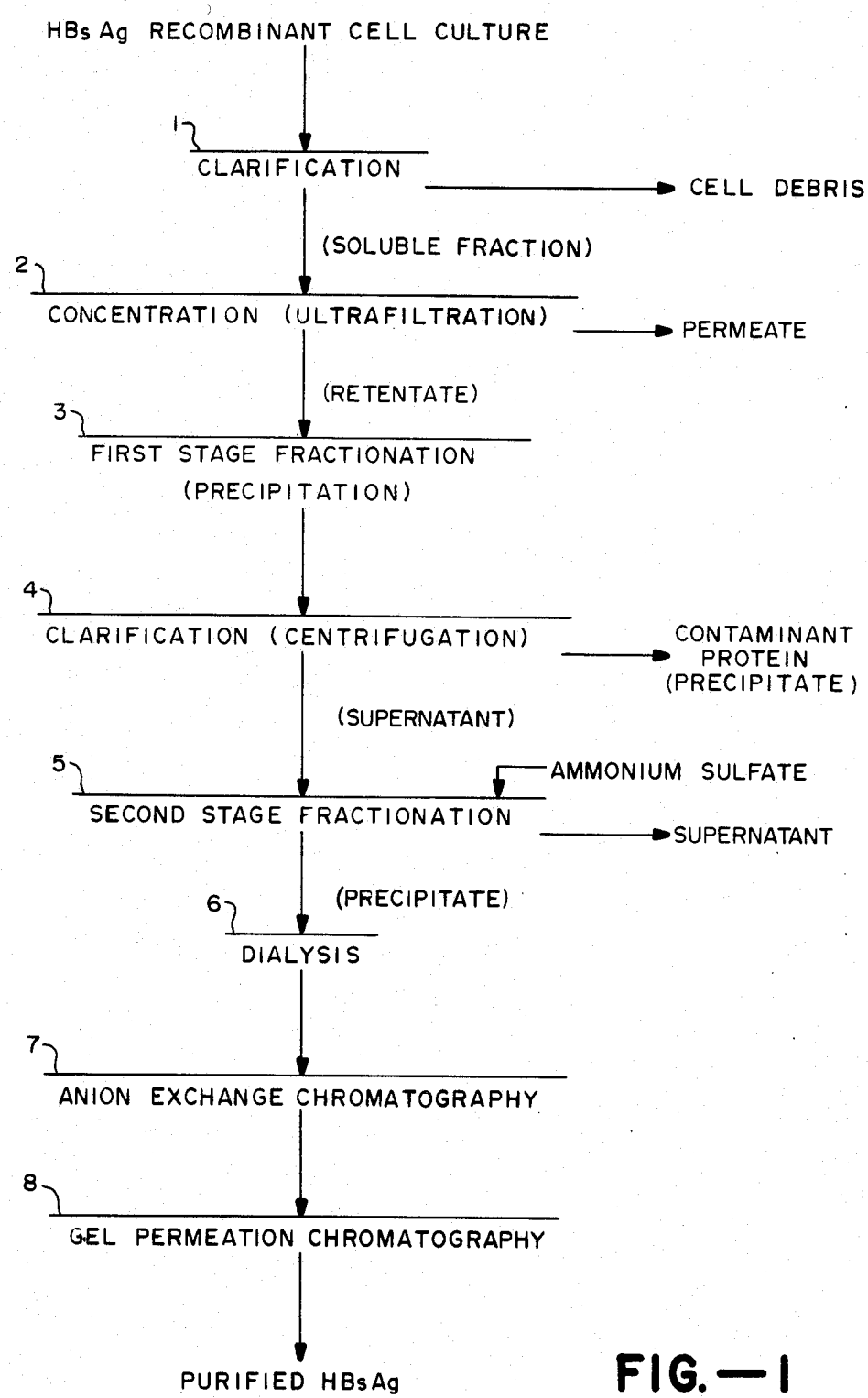
FIG.—1

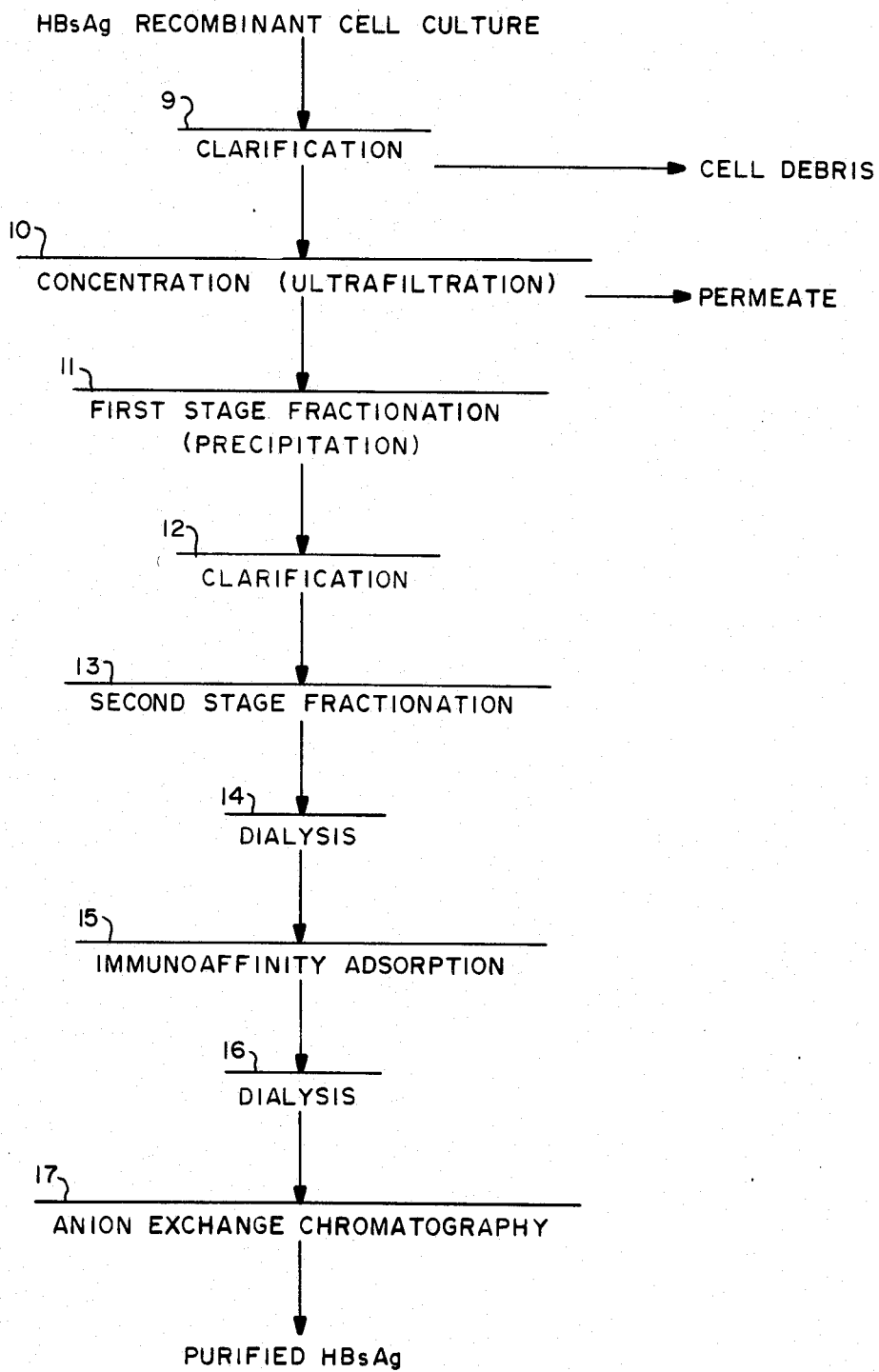
FIG.—2

PURIFICATION PROCESS FOR HEPATITIS SURFACE ANTIGEN AND PRODUCT THEREOF

BACKGROUND

The present invention relates to the purification of a protein produced by recombinant cells. Specifically, it provides a process for the efficient purification of hepatitis surface antigen (HBsAg) from cultures of recombinant cells producing this protein, particularly mammalian recombinant cells.

Viral hepatitis B is transmitted by carriers of hepatitis B through blood and body secretions. HBsAg has been purified from blood serum and made into a vaccine. Purcell, R. H. and Gerin, J. L. in *Viral Hepatitis*, The Franklin Institute Press (1978) p. 491 and Hilleman, M. R. et al ibid. p. 525. This publication describes a procedure for isolation of HBsAg in which the plasma from hepatitis B carriers is defribinated, and the HBsAg in the serum is (1) concentrated by ammonium sulfate precipitation, (2) subjected to isopycnic banding in a centrifuge using sodium bromide as the gradient medium, (3) subjected to rate-zonal sedimentation using a sucrose gradient, (4) inactivated with a variety of steps, (5) subjected to gel filtration, and (6) produced into a vaccine. Use of serum as a source for HBsAg is dangerous because of the presence of hepatitis B virus as well as the presence of as yet undefined adventitious agents. In addition, the techniques employed for purification of the HBsAg are time consuming and complicated. Formulation of hepatitis surface antigen for vaccine purposes has been performed by compounding with aluminum adjuvants such as aluminum hydroxide (op cit. Viral Hepatitis) and aluminum phosphate as described by Reerink-Brongers. E. E., et al, *Developments in Biological Standardization*, S. Karger (Basel, Switzerland) (1983) 54, 197.

Purification of a protein such as HGsAg produced in a recombinant cell may require different techniques from those which are used to purify HBsAg from "natural" sources such as blood serum due to the significantly different compositions of the two sources. Thus, one cannot predict that a technique used for purification of HBsAg from natural sources would be useful for purification of HBsAg from recombinant cell sources. Predictability is diminished even further where the final product must be exceptionally pure, e.g. for use as a human vaccine.

The present invention is directed to a process based upon chromatography which is successful in isolating HBsAg from recombinant cell cultures. A unqiue sequence of fractionation techniques is performed to produce HBsAg of high purity for use in human vaccine. This product is free of active adventitious agents.

SUMMARY OF THE INVENTION

In accordance with the present invention, a method of purifying HBsAg produced by culture of a recombinant cell provides a product of sufficient purity for incorporation into a vaccine. Cell debris is first separated from the cell culture medium which contains HBsAg. Clarified culture fluid containing HBsAg is then concentrated, preferably by ultrafiltration, and subjected to a two-stage fractionation by precipitation, preferably with ammonium sulfate, in which contaminant protein is removed in the first stage and HBsAg is precipitated in the second stage. The precipitated product is redissolved and dialyzed to remove salts. In one embodiment, applicable to HBsAg obtained from cell cultures without added serum, the dialyzed HBsAg solution is passed through an anion exchange bed to yield a HBsAg containing fraction. This fraction is then fractionated with respect to molecular weight, preferably by gel permeation chromatography, to produce a purified HBsAg product.

In an alternative to ion exchange fractionation followed by size fractionation, the fraction from the ammonium sulfate precipitation is purified by immunoaffinity adsorption. This alternative is applicable to isolation of HBsAg from either serum-free or serum-containing media. In a further alternative to this process, useful in certain instances, the fractionation by precipitation and dialysis steps need not be performed. The invention relates to HBsAg purified according to any of the above processes and to vaccines produced from this protein, particularly vaccines with superior antigenic properties to vaccines of the prior art.

BRIEF DESCRIPTION OF THE DRAWINGS

FIGS. 1 and 2 are flow diagrams of two methods of purification of HBsAg from recombinant cell culture.

DETAILED DESCRIPTION

A. Definitions

As used herein "hepatitis surface antigen" or "HBsAg" refers to the protein with the amino acid sequence of the surface antigen in any of its forms as encoded by the hepatitis B virus genome. Such form variations are included in the definition. In addition, as is well know, protein sequences are often modified by glycosylation, acetylation, or other chemical derivatization and may be associated with lipids. Finally, those proteins can exist in various states of aggregation, such as dimers, trimers, or even large aggregates with or without the aforementioned modification. These aggregates may include lipids. All of these are intended to be included within the definition of HBsAg.

As stated by Rutter, W. J. et al., EPO Patent Appln. Publ. No. 0072318, published Feb. 16, 1983, hepatitis B virus encodes the protein of hepatitis B surface antigen, which is 226 amino acids in length with a molecular weight of 22,000 Daltons. Hepatitis B surface antigen as isolated from the serum of chronic carriers of hepatitis B virus is a spherical particle with a diameter of 22 nm and a molecular weight of 2–4 million Daltons. This particle is thought to be composed of lipid and dimers of the hepatitis B surface antigen protein. However, the precise structure of the 22 nm particle is not well defined. HBsAg isolated from cultures of recombinant mammalian cells is in the form of 22 nm particles which are indistinguishable from those derived from serum as judged by standard laboratory tests. The surface antigen isolated from recombinant yeast also appears to be in the form of 22 nm particles (Valenzuela, P., et al., *Nature*, 298: 347 (1982)).

The designations of the techniques employed herein are used in the sense of their standard meanings. Thus, ultrafiltration refers to the technique whereby materials of low molecular weight, water, salts and some proteins, can be separated from those of higher molecular weight by providing a molecular sieve or filter with a pore size sufficiently small to retain larger molecular weight materials. Anion exchange chromatography refers to a technique whereby anionic materials can be adsorbed onto a support and subsequently eluted by the modification of solution conditions. Gel permeation chromatography refers to a molecular sieve process which separates a mixture of molecules according to size. Each of these individual techniques is known in the art as are the range of conditions under which they may be conducted.

B. General Method

B.1. Suitable Cell Cultures

HBsAg has been produced using a variety of microorganisms and tissue culture cells as recombinant hosts. Bacterial systems (European Publication No. 0020251, published Dec. 10, 1980), yeast systems (EPO Publ. No. 073657, published Mar. 9, 1983, and No. 0072318) and cell culture systems (EPO Publ. No. 0073656, published Mar. 9, 1983) have been used. HBsAg so produced has been shown to be immunogenic. See, e.g. EPO Publ. No. 0073656 (supra). It is particularly preferred to use a cell source which secretes the protein into the medium as this allows one to begin with a more pure starting material. However, if the desired protein is not secreted, lysis of the cells by standard means such as sonication, homogenization, or osmotic shock will succeed in freeing the HBsAg into the medium, and such purification method is applicable. In one embodiment of the invention, the medium for cell culture is a defined medium composed of specified vitamins, trace elements, and other nutrients to replace serum, thus eliminating a major source of contaminating protein. In another embodiment, serum is used in the medium.

B.2. Description of the Process

Referring to the flow diagram in FIG. 1, one procedure in accordance with the present invention is illustrated which is applicable to purification of HBsAg from a substantially serum-free culture. A modified procedure may be employed depending upon whether or not the starting culture contains serum. The description first will refer to the purification from cell culture medium without added serum.

Referring to step 1, the host cell debris, preferably in the form of non-disrupted host cells, is separated from supernatant fluid by a conventional solid-liquid separation technique such as filtration or centrifugation.

Referring to step 2, the soluble fraction is concentrated to a significant extent to permit an effective multi-stage precipitation fractionation as described in steps 3–5, infra. For that purpose, it is preferable to concentrate the HBsAg at least 25 to 30 fold, and to as high as 50-fold or more, in this step. Ultrafiltration is highly efficient for this purpose. Commercially available membranes fabricated from cellulose esters or polysulfone, for example, Amicon YM-30 and PM-10 and Dorr-Oliver C-30, may be used. A suitable molecular weight cut-off for the membrane is less than 100,000. Suitable operating pressures are on the order of 20 to 60 psi. The use of ultrafiltration membranes in a hollow fiber configuration such as a Romicon PM-100 and PM-10 have been used successfully for cell culture media which have serum added.

The retentate from ultrafiltration, step 2, is then fractionated by a two-step process as illustrated in FIG. 1, steps 3, 4 and 5. The ability to concentrate to the degree set forth above by ultrafiltration is a significant factor for obtaining good yields.

Referring to step 3, the first stage of the fractionation by precipitation is particularly effective for HBsAg produced from tissue culture, specifically CHO cells. A suitable first or preliminary precipitation step is performed by adding a protein-precipitating agent to the concentrate from step 2 to precipitate a first fraction of contaminant protein which is removed from the remainder of the solution by a suitable clarification technique such as centrifugation, filtration or the like. A particularly effective first stage fractionation is accomplished by adding sufficient solid ammonium sulfate to precipitate the desired amount of contaminant protein without precipitating the HBsAg. For this purpose, sufficient ammonium sulfate may be added to the concentrated cell culture at, for example, 4°–8° C. to produce a concentration of ammonium sulfate in the range of 20–30% of saturation, preferably 25%.

Referring to step 4, the contaminant protein precipitate is removed in a clarification step, suitably performed by centrifugation or by settling followed by filtration.

Referring to step 5, the supernatent fraction from clarification is subjected to a second stage of precipitation fractionation by increasing the ammonium sulfate level to an amount effective to precipitate substantially all of the HBsAg from the solution. The preferred technique to accomplish this is to increase the ammonium sulfate concentration to about 60% of saturation by adding additional ammonium sulfate. The product is precipitated and is collected by centrifugation for subsequent processing.

Other protein-precipitating agents may be utilized in place of the ammonium sulfate so long as they accomplish the objectives set forth above. In that regard, it has been found that polyethylene glycol, specifically, PEG 8000, may be utilized at a concentration of 2–4% w/v in step 3 and 8–10% w/v in step 4.

Referring to step 6, the precipitate is redissolved and dialyzed to remove salts in preparation for fractionation by anion exchange chromatography, step 7. Dialysis is performed to remove salts which would interfere with such anion exchange chromatography. This step may be performed by dissolving the precipitate in dilute buffer, preferably at a pH of about 6–8, and dialyzing at a low temperature against dilute buffer primarily to remove the ammonium sulfate. An appropriate buffer comprises 1–50 mM Tris-Cl or sodium phosphate, preferably about 10 mM Tris-Cl. Other methods for salt removal may also be employed such as gel filtration or diafiltration.

Referring to step 7, the solution is subjected to a further fractionation by using an anion exchange resin. Suitable resins for this purpose include DE-Sepharose (Pharmacia, Inc.), DE-Trisacryl (LKB-Produktor), and DE-52 cellulose (Whatman Inc.). The preferred resin is DE-52 cellulose (Whatman Inc.). The conditions for performing the separation or fractionation are chosen to be suitable for the particular resin. In general, the resin is used in a column. A pH of 7.5 using a 10 mM Tris-Cl buffer is particularly effective. The product from step 6 is passed through the column containing sufficient resin to adsorb all of the HBsAg. When using DE-52 cellulose and HBsAg produced by cell culture in the absence of serum, a ratio of about 1 mL of packed resin per 14 mg protein in the dialyzed ammonium sulfate fraction from step 6 is suitable.

After adsorption on the column, a gradient elution system is used preferably to differentially remove the adsorbed HBsAg from the resin. Suitable changes in the pH, salt concentrations, or temperature would be apparent to workers in the field. A suitable eluant for HBsAg on DE-52 cellulose includes a sodium chloride-based gradient ranging from 0 to 0.3M.

After step 7, fractions containing HBsAg protein are pooled for size fractionation, preferably by gel permeation chromatography. The identity of such fractions can be ascertained by any appropriate assay procedure for HBsAg. One technique is polyacrylamide gel electrophoresis in the presence of sodium dodecyl sulfate (SDS-PAGE) described by Laemmli, *Nature*, 227: 781 (1970). Visualization of the SDS-PAGE is achieved by staining with silver chloride by the method of Merrill, et al., *Science*, 221: 1437 (1981). It is preferable to pool only those fractions containing HBsAg which are low in high molecular weight contaminant protein as judged by the foregoing SDS-PAGE procedure, as a subsequent step appears to remove proteins of molecular weight in excess of 60,000 only with difficulty.

Referring to step 8, the HBsAg-containing fractions from anion exchange chromatography are subjected to size fractionation by gel permeation chromatography. Suitable gels include Biogel A-5m (Bio-Rad) or Sepharose CL-6B (Pharmacia). The quantity of the gel required depends upon the nature of the gel. A suitable amount of Biogel A-5m or Sepharose CL-6B is approximately 1 liter of resin column per 150-200 mg HBsAg. Gel permeation chromatography is carried out at a temperature of about 2° C. to 8° C., preferably about 4° C. in a buffer solution at a pH of 6-9 with a NaCl concentration of between 0.5-1M.

The same SDS-PAGE technique may be used to assay HBsAg in the fractions obtained by gel permeation chromatography which are to be pooled. The overall purification of HBsAg from serum-free cell culture fluid is approximately 50 fold. The overall yield is about 40 percent. Analysis of the purified fraction by SDS-PAGE typically shows the presence of both glycosylated and non-glycosylated forms of the hepatitis B surface antigen protein. Examination of the preparation by electron microscopy shows the presence of particles in the size range of 20-25 nm.

The purity of the HBsAg product is in excess of 98 percent free of other proteins and it is essentially free of DNA as measured by currently available techniques.

Referring to FIG. 2, alternate procedures are illustrated which are suitable for use with HBsAg culture media, whether or not they contain serum. Steps 9–14 are performed in the same manner shown in FIG. 1 as steps 1–6.

In step 15, the solution from step 14 is purified by passage through an immunoaffinity absorbent column containing monoclonal antibodies specific for HBsAg. The HBsAg is adsorbed on the column and the contaminants either flow through the column or are washed off. Thereafter the adsorped HBsAg is desorbed by passing an appropriate eluent through the column.

An appropriate immunoaffinity adsorbent column for use in step 15 is formed by covalently coupling a monoclonal antibody specific for HBsAg to a cross-linked agarose such as Sepharose CL-2B (Pharmacia, Inc.) with carbonyldiimidazole using the method of Bethell, G. S. et al., *J. Biol Chem.* 254, 2572 (1979). HBsAg can be obtained in a nearly homogenous form by a single passage through this immunoaffinity adsorbent column from crude cell culture fluid obtained from the culture of mammalian cells in the presence of animal serum.

After passage of the crude culture fluid through the column, an appropriate buffered eluent such as 10 mM Tris-Cl at a pH of 7.5 containing 1.0M sodium chloride is used to wash the column. The bound HBsAg is released from the adsorbent by an appropriate eluent (e.g. 0.1M sodium acetate/acetic acid pH 4.0 containing 1.0M NaCl, or 10 mM Tris-Cl pH 7.5, containing 1.0M NaCl, 3M KSCN).

In step 16, the eluent from the immunoaffinity column preferably is dialyzed or diafiltered against a suitable medium such as 10 mM Tris-Cl pH 7.5, containing 0.18M NaCl. Dialysis may be performed in a manner similar to that used in step 6. Diafiltration may be performed with an Amicon PM-10 or YM-30 membrane.

In step 17, the product from step 16 is subjected to anion exchange chromatography. A suitable technique is by passage over a column of DE-52 which is washed with 10 mM Tris-Cl at pH 7.5 containing 0.18M NaCl. The eluent and wash are combined to form the purified product.

In another embodiment, steps 11–14 may be eliminated for some cell cultures.

B.3 Pharmaceutical Composition

HBsAg purified according to the present invention can be formulated according to known methods to prepare pharmaceutically useful compositions, whereby the HBsAg is combined in admixture with a pharmaceutically acceptable carrier vehicle. Suitable vehicles and their formulation are described in Remington's *Pharmaceutical Science*, E. W. Martin, ed; incorporated herein by reference.

B.4 Vaccine Preparation

The vaccines of the present invention, incorporating HBsAg purified as described herein, can be prepared according to known methods, wherein the HBsAg is combined in admixture with a suitable vehicle. Suitable vehicles include various known adjuvants. Such vaccines contain an effective amount of HBsAg and a suitable amount of vehicle in order to prepare a vaccine for effective administration to the host.

A particularly effective vaccine is produced by compounding HBsAg with aluminum salts in the form of a gel as an adjuvant. The gel may be formed in situ by mixing a sufficient amount of HBsAg with a sufficient amount of a soluble aluminum salt such as potassium aluminum sulfate (e.g. at pH 3.5) and then coprecipitating the aluminum salt with HBsAg by titration of the solution with a basic titrant to a higher pH (e.g. 5 to 7) to form the gel. Such basic titrants may be an alkali hydroxide, such as sodium hydroxide, or alkali salts such as sodium phosphate. As defined herein, the "aluminum hydroxide adjuvant" means an adjuvant for the HBsAg vaccine of the present invention containing aluminum primarily as the hydroxide in a formulation suitable for injection; while the term "aluminum phosphate adjuvent" means an adjuvant for the HBsAg vaccine containing aluminum primarily as the phosphate in a formulation suitable for injection. It has been found that the aluminum phosphate adjuvant vaccine has superior antigenic properties compared to those of the aluminum hydroxide adjuvant vaccine and that both of these have superior properties to that of a commercial serum-based vaccine, Heptavax B, based upon intraperitoneal injection of mice.

Because of the unique methods by which the active component of these vaccines are produced, vaccines hereof are likely to be essentially free of extraneous protein(s), viral and cellular components, and DNA. Therefore, they are less likely to produce the complications of virus vaccine preparations made from serum.

It has further been found that the vaccine of the present invention has vastly superior antigenic properties in chimpanzees than Heptavax B as reported in Hillman, M. R., et al, *Viral Hepatitis,* International Symposium, The Franklin Institute Press (1978), 525. These results are believed to be due, in major part, to a method of purification used in the present invention compared to the relatively harsher purification methods reported for production of HBsAg used in Heptavax B. Specifically, the present methods avoid harsh proteases and protein denaturants of those reported methods. Although the vaccine of the present invention which was compared was purified in the manner set out in FIG. 1, it is believed that the alternative purification methods herein would provide similar improvements in result.

The following process and results are intended to exemplify, but not limit, the invention.

C. Example 1

This example illustrates the procedure of FIG. 1 (steps 1–8). Cell culture fluid is obtained from cell cultures of Chinese hamster ovary cells in roller bottles in the absence of serum.

The culture fluid is filtered through a 0.22 micron Sartorius filter fabricated from cellulose acetate and cellulose to remove cells and cell debris which arise during cell culture. Approximately 100 L of cell culture fluid is rapidly filtered through 2 square feet of membrane.

Clarified cell culture fluid is concentrated by ultrafiltration using a Dorr-Oliver system with a C-30 membrane fabricated from cellulose esters. The system is composed of a filtration press to hold the membranes, a pump for recirculation of the fluid to be concentrated, and a pressure vessel for a reservoir. The cell culture fluid is concentrated and the retentate is drained from the system. The system is flushed twice with 0.5 L of purified water which is combined with the retentate to effect a quantitative recovery of HBsAg. The washes are pooled with the retentate. A permeate rate of approximately 3–6 L/hr/sq ft is achieved.

Concentrated cell culture fluid is fractionated in two steps. Sufficient solid ammonium sulfate is added to the concentrated cell culture fluid at 4°–8° C. to produce a concentration of 25% saturation (706 g/L is used as 100% saturation at 4° C.). The solution is clarified by centrifugation at 6000 g for 20 minutes. The pellet is discarded and the supernatant is brought to 60% saturation in ammonium sulfate. The second-stage pellet is collected by centrifugation at 6000 g for 20 minutes.

The yield on ammonium sulfate fractionation is dependent on the concentration factor achieved by ultrafiltration. A concentration factor equal to or greater than 35 typically achieves a maximal yield for the step. Above a concentration factor of 35, there is no substantial increase in the yield on ammonium sulfate fractionation.

The second-stage pellet from the ammonium sulfate fractionation is dissolved in 10 mM Tris-Cl pH 7.5 (pH measured at room temperature) in a volume in mL approximately equal to 0.25 times the original culture medium volume in liters. The solution is dialyzed at 4° C. against 10 mM Tris-Cl, pH 7.5. to remove the ammonium sulfate. The combination of ultrafiltration, ammonium sulfate fractionation and redissolution of the pellet results in a concentration factor of approximately 2000 fold based on the volume of starting cell culture medium.

Whatman DE-52 cellulose packed into a column is used to fractionate the dialyzed 60% ammonium sulfate fraction. The conditions of chromatography are as follows. The resin is equilibrated to a pH of 7.5 using a 10 mM Tris-Cl buffer. The gradient used for elution is linear over the range of 0–0.3M NaCl. HBsAg elutes as a partially resolved peak on the leading edge of the peak respresenting the elution of the bulk of the protein from the column.

The HBsAg fractions from the DE-52 cellulose anion exchange chromatography are pooled and processed in the next step by gel permeation chromatography. The step yield after DE-52 cellulose is 50 percent which does not include an additional recovery by the reprocessing of HBsAg containing fractions not pooled due to insufficient purity. The pooled fractions are concentrated with a stirred cell (Amicon) using a YM-30 membrane at a pressure of 25 psi. A flux of approximately 1 L/hr/sq ft is obtained.

The concentrated HBsAg fraction from the DE-52 cellulose column is applied to a column of Sepharose CL-6B resin. The product from 200 L of cell culture fluid (approximately 100 mg HBsAg) can be processed with a 0.5 L column of Sepharose CL-6B. The column is run at 4° C. in a solution of 10 mM Tris-Cl pH 7.5 containing 1.0M NaCl (pH measured at room temperature).

The overall yield for the process is approximately 35%.

The product from step 8 or step 17 is adjusted to a concentration of approximately 0.2 mg/mL by eight dilution or concentration by ultrafiltration using for example an Amicon stirred cell with a PM-10 or YM-30 membrane. The resulting solution is filtered through a 0.22 micron filter and is heated at 60° C. for a period of from 3 to 10 hours.

The HBsAg was formulated into a vaccine by compounding with aluminum salts in the form of a gel as adjuvant as follows. 20 μg of HBsAg is mixed with 0.1M NaCl and 0.88% w/v alum and 0.05% w/v Thimerosal as a preservative. The solution is then titrated to a pH of between 5–7 (5.5) with a 0.1M sodium phosphate at pH 12. Each ml of adjuvant-vaccine contains 0.5 mg equivalent $Al^{+3}$ ion, 20 μg HBsAG and 0.05% w/v Thimerosal.

C. Product Characterization

It is estimated that there is less than 20 pg of DNA per mg of HBsAg produced by the procedure described in this report. This value was determined using the clearance factor by the process for DNA of one million, a concentration of HBsAg in the cell culture fluid of 1 mg/L and an amount of DNA per liter of cell culture fluid of 20 μg as estimated by dot-blot hybridazation. Direct measurement of DNA in the product by dot-blot hybridization shows that there is less than 10 pg of DNA per mg of HBsAg.

No significant decrease in stability of the HBsAg product at 4° C. was observed over a period of six months. A solution composed of 0.025 mg/mL HBsAg purified by the procedure outlined, 10 mM Tris-Cl; pH 7.5, and 0.15M NaCl can be heated at 60° C. for a period of 10 hours with negligible loss as measured by both ELISA and Abbott AUSRIA II assays.

The HBsAg is further characterized by a purity of greater then 98% as indicated by SDS-PAGE.

Example 2

This example illustrates the purification of HBsAg from a cell culture medium containing serum by the procedure shown in FIG. 2.

The concentration of serum added to the cell culture fluid may range from 0-7.5% v/v. Steps 9-14 of this example are essentially the same as steps 1-6 described in Example 1 with the exceptions noted below.

In step 10, the cell culture fluid containing serum is concentrated by ultrafiltration using a Romicon hollow fiber system with a PM-100 or PM-10 type membrane. The ultrafiltration process is performed at ambient temperatre at a pressure up to 25 psi. The cell culture fluid is concentrated and the retentate is drained from the system. The system is flushed with purified water which is combined with the retentate to effect a quantitative recovery of HBsAg. A permeate rate of 6-10 L/hr/sq ft is achieved with a PM-100 type membrane with a cell culture medium which contains 7.5% serum. A concentration factor equal to or greater than 20 for cell culture fluids containing equal to or greater than 1% v/v added serum is required to achieve the optimum yield in the subsequent purification step.

The concentrated cell culture fluid is fractionated with ammonium sulfate as described in Example 1.

In step 13, HBsAg is precipitated by ammonium sulfate as in step 5 of Example 1. In step 14, the product is dialyzed as in step 6 of Example 1. The dialysis medium is 10 mM Tris-Cl pH 7.5 containing 1.0M NaCl and the dialysis is performed at 2°-8° C.

In step 15, the dialyzate is applied to an immunoaffinity column and the column is washed with 10 mM Tris-Cl PH 7.5 containing 1.0M NaCl. The HBsAg bound to the column is eluted with a solution of 0.1M sodium acetate pH 4.0 containing 1.0M NaCl. The procedure is performed at refrigerated temperature (2°-8° C.) or at room temperature without any signficant difference.

In step 16, the eluent from step 15 is dialyzed against 10 mM Tris-Cl containing 0.18M NaCl. Alternatively, the eluent is diafiltered using an Amicon YM-30 or PM-10 membrane against the same buffer.

In step 17, the dialyzed eluent is passed through a DE-52 column. HBsAg is not bound by DE-52 in this medium. The column is washed with 10 mM Tris-Cl pH 7.5 containing 0.18M NaCl to effect a quantitative recovery of the HBsAg. Approximately 1 mL of DE-52 is used per 10-20 mg of HBsAg.

The overall yield of HBsAg for Example 2 is approximately 80%. The purity of the product produced by either the process described in Example 1 or Example 2 is comparable.

Example 3

The aluminum phosphate adjuvant vaccine of Example 1 was compared with (a) an aluminum hydroxide adjuvant vaccine formed by substituting sodium hydroxide for sodium phosphate in the procedure, and (b) commercial Heptavax B supplied by Merck, Sharp and Dohme in a mouse potency assay. The results shown in the following Table 1 demonstrate the increased potency of the claimed vaccine relative to a commercial preparation.

TABLE 1

| | MOUSE POTENCY ASSAY[a] | | |
|---|---|---|---|
| | Percent Seroconversion (Seropositive/Total Mice[b] × 100) | | |
| Dose | | cell culture vaccine | |
| (μg) | Heptavax B | aluminum hydroxide | aluminum phosphate |
| 0.030 | 5 | 20 | 75 |
| 0.156 | 55 | 85 | 95 |
| 0.625 | 85 | 85 | 100 |
| 2.5 | 90 | 95 | 100 |
| 10 | 90 | 95 | 100 |
| ED$_{50}$[c] | 1.50 μg | 0.093 μg | 0.039 μg |
| relative potency | 1.0 | 1.6 | 3.8 |

[a]Mice were injected intraperitoneally with 1 mL of vaccine containing an aluminum gel adjuvant. 28 days after injection, the mice were exsanguinated and the plasma fraction was tested for the presence of anti-HBs antibodies by Ausab radioimmunoassay (Abbott Laboratories).
[b]20 mice per group.
[c]ED$_{50}$ is the estimated dose of vaccine at which 50% of the mice become seropositive.

What is claimed is:

1. A process for purifying HBsAg having 226 amino acid residues, comprising the steps of:
   (a) separating the HBsAg from host cell debris in a recombinant cell culture medium producing the HBsAg,
   (b) concentrating the separated HBsAg from step (a) by ultrafiltration,
   (c) adding ammonium sulfate to the concentrate from step (b) to an ammonium sulfate concentration of about 60% of saturation,
   (d) redissolving the precipitated HBsAg from step (c),
   (e) passing the separated HBsAg through an immunoaffinity adsorbent column containing monoclonal antibody specific for HBsAg to adsorb the HBsAg and remove contaminants,
   (f) releasing the adsorbed HBsAg by passing an eluent through the column, and
   (g) fractionating the HBsAg in said eluent by passing the same through an anion exchange bed to yield at least one purified HBsAg-containing fraction.

2. The process of claim 1 wherein the eluent of step (f) contains sodium acetate/acetic acid.

* * * * *